United States Patent [19]

Gudnason et al.

[11] 4,288,551

[45] Sep. 8, 1981

[54] PROCESS FOR THE PURIFICATION OF SUGAR SYRUPS

[75] Inventors: Geir V. Gudnason, Atlanta; Joseph E. Stell, Douglasville, both of Ga.

[73] Assignee: The Coca-Cola Company, Atlanta, Ga.

[21] Appl. No.: 128,683

[22] Filed: Mar. 10, 1980

[51] Int. Cl.[3] .......... C13D 3/00; C12P 3/00

[52] U.S. Cl. .......... 435/168; 127/48; 127/57; 435/276; 435/818

[58] Field of Search .......... 127/48, 57; 435/274, 435/276, 168

[56] References Cited

U.S. PATENT DOCUMENTS

| | | | |
|---|---|---|---|
| 3,479,221 | 11/1969 | Buhl | 127/48 X |
| 3,530,067 | 9/1970 | Friedman . | |
| 3,705,098 | 12/1972 | Shepherd . | |
| 3,847,803 | 11/1974 | Fisk . | |
| 3,853,616 | 12/1974 | Rundell | 127/48 |
| 3,909,287 | 9/1975 | Rundell . | |
| 3,926,662 | 12/1975 | Rundell | 127/48 |
| 3,959,131 | 5/1976 | Ramirez . | |
| 3,975,269 | 8/1976 | Ramirez . | |
| 4,021,338 | 5/1977 | Harkin . | |
| 4,076,552 | 2/1978 | Farag | 127/48 X |
| 4,081,288 | 3/1978 | Torres . | |
| 4,196,017 | 4/1980 | Melville | 127/48 X |

FOREIGN PATENT DOCUMENTS 2446511 4/1976 Fed. Rep. of Germany .

OTHER PUBLICATIONS

Meade-Chem, "Cane Sugar Handbook", Tenth Edition, pp. 128,129, 1977.

Processed Prepared Food, p. 120, May 1979.

White et al., "Principles of Biochemistry," 2nd Edition, pp. 259-260, 343-345, 1959.

*Primary Examiner*—Sidney Marantz

*Attorney, Agent, or Firm*—Birch, Stewart, Kolasch & Birch

[57] ABSTRACT

A process for removing color, turbidity, flavor, and odor from impure sugar syrups by entrapping the sugar impurities in an insoluble, primary calcium phosphate or aluminum hydroxide floc at about neutral pH, adding a suitable amount of hydrogen peroxide, rapidly decomposing the hydrogen peroxide with catalase to form a quantity of oxygen bubbles, and, during bubble formation, adding a polyelectrolyte to convert the primary floc into a secondary floc in which the oxygen bubbles are entrapped thereby causing flotation. The purified sugar syrup is then filtered with or without activated carbon and small amounts of a filter aid to produce a sugar syrup with substantially reduced color, turbidity, flavor, and odor.

62 Claims, 1 Drawing Figure

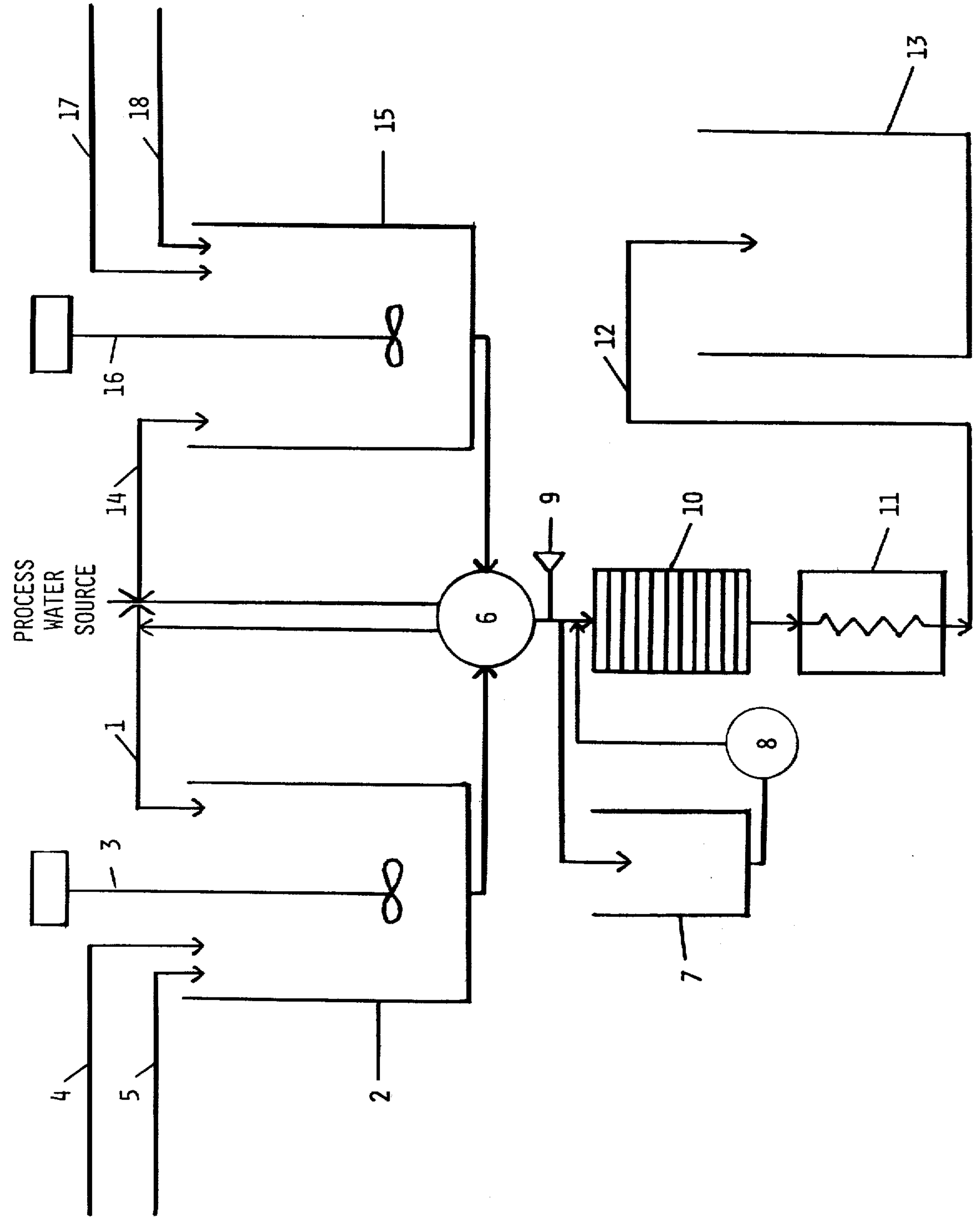
PROCESS
WATER
SOURCE
1
2
3
4
5
6
7
8
9
10
11
12
13
14
15
16
17
18

PROCESS FOR THE PURIFICATION OF SUGAR SYRUPS

BACKGROUND OF THE INVENTION

This invention relates to a process for the purification of unrefined sugar solutions. More specifically, it relates to a process for removing turbidity, color, flavor, and odor from impure sugar solutions which may or may not be subjected to further crystallization.

The prior art is primarily concerned with the purification of either raw cane juice or raw sugar syrups, each of which are subsequently crystallized to yield raw sugar (mill sugar) and refined sugar, respectively, leaving in the water phase a great many of the impurities.

In the manufacture of raw sugar (mill sugar), the dark colored raw cane juice, containing gums, waxes, proteins, organic acids, minerals, and particles of vegetable material, is first treated by adding lime to the hot juice. The lime reacts with the organic acids in the juice and forms an insoluble floc with various colloids and with the phosphates in the juice. The floc, containing many impurities, is usually allowed to settle to the bottom of the reaction vessel. Alternatively, the floc may be flotated, in which case more lime and phosphoric acid, or any one of a number of soluble phosphate salts well known to those skilled in the art, may be added to increase the amount of floc. See "Cane Sugar Handbook", Meade and Chen, John Wiley and Sons, New York, 1977, p. 129, and references therein, each of which references is herein incorporated by reference. Polyelectrolytes are usually added to increase the size of the floc particles, and this "secondary" floc is then conventionally flotated by aeration, employing nozzle injection systems, high speed pumping or agitation. The floc-flotation-clarified cane juice is then evaporated in a multi-effect vacuum evaporator and crystallized in a vacuum pan. The mixture of sugar crystals and sugar syrup, or massecuite, is subsequently centrifuged to remove most of the dark mother liquor, or molasses, from the crystals. Residual molasses remaining on the crystals may then be removed with a water spray during continuing centrifugation. The greater the volume of wash water used to wash the crystals, the purer the resulting mill sugar will be. On the other hand, the more water is used, the more the sugar crystals will dissolve, thus reducing the yield of mill sugar. However, no matter how well the crystals are washed, they will most likely contain impurities occluded within the crystals. These impurities could be reduced by using more lime and phosphoric acid in the flocculation step, but again, at the expense of yield. Thus, even the best raw sugars (mill sugars) are likely to contain various impurities.

Such mill sugars are suitable for many products such as candy, bakery products, or as sweeteners for coffee or tea, but not for soft drinks, where the color, aroma, flavor, and turbidity of the sugar may affect the character of the soft drinks and shorten their shelf life. Many sugar mills produce so-called "sulfitated" sugars, wherein the cane juice is treated with sulfur dioxide prior to evaporation. These sugars often have a white appearance, which makes them suitable for certain uses, even though the aroma, flavor, and turbidity may not have been significantly reduced by this treatment. Mill sugar made with other special processing steps, such as extra washing, is called "mill white" or "plantation white," and is also suitable for certain uses. Generally, however, neither sulfitated sugar nor plantation white sugars are pure enough for use in soft drinks, in which higher quality refined sugars are necessary.

In manufacturing refined sugar, crystalline raw sugar, containing a number of undesirable nonsugar constituents, is first washed with water to remove any adhering syrup. The syrup that is washed off the crystals is similar in nature to raw cane juice and is treated separately to recover the sugar from it. The washed sugar is dissolved in water, and the resulting syrup is then clarified by flocculation. The clarified syrup is then decolorized with activated carbon, bone char or other appropriate decolorizing substances to give a purified "fine liquor." The fine liquor is then crystallized to yield refined sugar. The degree of refinement depends on the number, and effectiveness, of the flocculation and decolorization steps.

The flocculation steps usually involve addition of lime and a phosphate ion source, such as phosphoric acid, to the liquor to form a calcium phosphate floc. This floc is conventionally removed by air flotation, often with the addition of a polyelectrolyte in order to form a so-called secondary floc and thereby increase the size of the floc particles. Decolorization of the clarified liquor is usually accomplished by passing it through columns of bone char before the final crystallization.

Soft drink manufacturers virtually always require refined sugar for use in their beverages. However, many countries do not have sufficient refining capacity, and in such countries only mill sugars may be available to certain industries. Before using such mill sugars for soft drinks it is necessary to remove from them the turbidity, color, flavor, and odor, and this must be done in the bottling plant itself.

Various methods for in-plant purification of mill sugar are in use around the world. The simplest method is to prepare a mill sugar syrup and to filter the syrup cold with a small amount of filter aid through a filter press. Such filtration only removes insoluble matter, and does not decolorize or remove flavor and odor. Treatment of hot sugar syrup with activated carbon and subsequent filtration with filter aid is another method currently in use. This process removes turbidity, flavor, aroma, and much of the color, depending on the amount of carbon used. The process has found much favor in bottling plants, but when the sugars are very impure, very large amounts of carbon and filter aid are required in order to bring the sugar syrup up to acceptable purity standards. In addition, the more carbon and filter aid are used, the slower the rates of filtration, and this reduction in production rates may interfere with plant schedules.

Another in-plant purification process presently used includes continuously centrifuging hot syrup to remove turbidity, and subsequently passing the syrup through granulated carbon columns to remove color, odor, and flavor. However, centrifuging is relatively inefficient for turbidity removal, and the degree of color removal in such columns is often not very efficient because the carbon used must be rather coarse in order to allow a sufficiently rapid flow through the column. In addition, because of its gradual loss of decolorization ability, the carbon must be replaced periodically. Still other purification processes involving ion exchange columns are used in some large bottling plants. The ion exchange resins are extremely efficient in removing color, but only if all turbidity has previously been removed, e.g., by filtration with a filter aid. In addition, the ion exchange process is not efficient in removing odor and flavor.

Purification processes involving entrapment of sugar impurities in a chemical floc and subsequent removal of the floc are in use in sugar mills and in refineries, but, almost never in bottling plants.

The floc clarification process consists of adding to the dissolved, usually hot, sugar syrup small amounts of lime and phosphoric acid, or lime and soluble phosphate salts or aluminum sulfate. At about neutral pH the lime and phosphate or aluminum sulfate form an insoluble, calcium phosphate or aluminum hydroxide floc (primary floc) which contains insoluble matter, some of the colloids, and much of the color. The floc cannot be conveniently filtered because of its gelatinous nature. It will settle if given enough time, but it does not compact well enough to obtain a satisfactory yield of clarified syrup. Centrifuging in a continuous centrifuge is not satisfactory either, especially at high sugar concentrations (50°-60° Brix), probably because the turbulence in the centrifuge breaks the floc particles into smaller particles of a density about the same as or less than the syrup, so that a significant amount of floc is left in the syrup after centrifugation. An aluminum hydroxide floc is significantly more difficult to remove from high Brix syrups by centrifuging than calcium phosphate floc.

The most efficient method for removing the primary calcium phosphate or aluminum hydroxide floc is by flotation with a gas. Usually, with either type of floc, a polyelectrolyte is added to form a more easily flotatable secondary floc. The aluminum hydroxide floc is less preferred for use in flotation in high Brix syrups than phosphate floc because it rises more slowly, forms a looser scum, and leaves some floc in suspension. It is possible, however, to obtain satisfactory flotation in high Brix syrups with aluminum hydroxide floc at the expense of very high sugar losses. Thus, aluminum hydroxide is generally not suitable for use in clarification of high Brix sugar syrups. However, aluminum hydroxide may be effectively flotated to clarify low Brix syrups (up to 30° Brix) even at room temperatures.

Flotation of the secondary floc is accomplished by aeration, either by vigorous agitation or aeration with powerful, high shear centrifugal pumps equipped with air inlets. Mechanical aeration, although suitable for refineries, is less suited for bottling plants because of the capital expense of the extra equipment needed and the added utility costs. Further, the aeration step for an average batch may take 15-120 minutes to complete, depending on the size of the pump, thus intefering with plant schedules.

Floc flotation depends on gas bubbles adhering to the floc, and it is known that bubbles of air adhere rather strongly to the primary flocs of calcium phosphate or aluminum hydroxide, and even more strongly to their secondary flocs (produced through the use of a polyelectrolyte). On the other hand, bubbles of oxygen gas, which can be easily generated from hydrogen peroxide by catalase, do not adhere to either the primary or secondary flocs, making the use of oxygen bubbles in flotation seemingly impossible.

It would be of great benefit, therefore, to develop a process for floc flotation which would avoid the capital expense and power costs associated with conventional aeration, and which would overcome the seeming impossibility of using enzymatically generated oxygen gas bubbles to flotate sugar syrup flocs.

SUMMARY OF THE INVENTION

It has now been found that the disadvantages associated with in-plant sugar flotation processes can be overcome by using an improved secondary floc flotation process wherein the improvement comprises utilizing oxygen bubbles, generated from hydrogen peroxide by catalase, for secondary floc flotation instead of the conventional aeration procedure. The invention provides an improved process for purifying impure sugar syrups by adding to the syrup a suitable amount of a phosphate ion source (such as a soluble calcium phosphate or phosphoric acid), adding lime to form a primary floc, adding a suitable amount of hydrogen peroxide, adding small amounts of a catalase preparation, which immediately produces copious amounts of oxygen bubbles evenly dispersed throughout the syrup, and then adding a small amount of a polyelectrolyte to capture the oxygen bubbles in a secondary floc, thereby causing the secondary floc to rise to form a well-packed scum. The purified syrup may then be easily and rapidly filtered with or without addition of small amounts of carbon and filter aid.

With floc flotation either by air or by oxygen bubbles, much decolorization and removal of turbidity takes place. However, an advantage of the oxygen flotation method is that significantly more decolorization takes place in oxygen flotation than in air flotation. Small amounts of activated carbon may be added before the floc flotation to further reduce color, flavor, and aroma. The carbon will be contained in the flotated scum.

A further important advantage of the process is that complete aeration with oxygen bubbles takes only 1-2 minutes since all the bubbles are formed at once throughout the syrup, whereas mechanical aeration involves pumping the entire amount of syrup once or more, and may take from 15 to 20 minutes. A further advantage of the process of the invention is that the primary floc is not broken up after it is formed so that flotation can take place almost immediately after aeration, whereas during the turbulent pumping needed for mechanical aeration, the primary floc is completely broken up and must be given time to reform.

BRIEF DESCRIPTION OF THE DRAWING

The drawing is a schematic representation of a floc flotation apparatus suitable for use in conjunction with the practice of this invention.

DETAILED DESCRIPTION OF THE INVENTION

A complete understanding of the invention, including the best mode of operation thereof, will be gained by those skilled in the art from the following discussion taken in conjunction with the following Examples and the drawing.

EXAMPLES OF THE INVENTION

The following Examples illustrate the invention. Unless otherwise indicated, the polyelectrolyte used is Magnifloc 846A, a polyacrylamide polyelectrolyte manufactured by Americn Cyanamid and added as a 0.1% aqueous solution, and all catalase is Takamine Catalase-L, a beef liver catalase in a stabilized form, manufactured by Miles Laboratories, Inc. In addition, unless indicated to the contrary, lime, phosphoric acid, aluminum sulfate, polyelectrolyte and carbon are added as a specified amount (wt% or ppm) of the weight of sugar present in the solution (syrup); and hydrogen peroxide and catalase are added as an amount (in ppm) based on volume of syrup. Finally, in the examples which follow, the quality of the sugar is expressed in Reference Base Units (RBU's), which are determined for the syrup, and are calculated as follows:

$$RBU = \frac{A_{420\ nm} - 2(A_{720\ nm})}{b \times c} \times 1000$$

Where b is cell length in cm and c is sugar concentration in g/ml.

In order to demonstrate the relative affinity of oxygen and air for primary floc and secondary floc (after polyelectrolyte addition), the following experiment was performed.

EXAMPLE 1

To about 1200 ml of a 60° Brix solution of refined sugar at 70° C. were added 0.1% pure lime and 0.09% of 100% phosphoric acid, both based on weight of sugar. The pH of the resulting syrup was 6.3. In about 5 minutes a primary calcium phosphate floc had completely formed. The primary floc-containing syrup was then divided into six portions of 200 ml each and placed into separatory funnels.

Three of the samples were then aerated by vigorous shaking: the first one after adding and mixing 12 ppm of Magnifloc 846A with the syrup; the second just before adding and mixing 12 ppm of the polyelectrolyte; and the third with no polyelectrolyte added.

The other three samples were aerated by adding 120 ppm of hydrogen peroxide and 23 ppm of catalase (both based on syrup volume) to the syrups: the first without polyelectrolyte; the second, about one minute before adding the polyelectrolyte; and the third, after adding and mixing the polyelectrolyte with the syrup.

The flocs in these samples behaved as shown in Table 1.

TABLE 1

| | No Polyelectrolyte Added | Aeration Before Polyelectrolyte | Aeration After Polyelectrolyte |
|---|---|---|---|
| With Air Bubbles | Good Flotation | Good Flotation | Good Flotation |
| With Oxygen Bubbles | No Flotation | Good Flotation | No Flotation |

The results shown in Table I demonstrate that, whereas air bubbles have a physical affinity for both primary and secondary floc particles, the oxygen bubbles have affinity for neither, but rather must be captured in a secondary floc (formed by addition of polyelectrolyte) in order to flotate the floc.

In order to demonstrate the effect of temperature and amounts of added catalase on flotation, the following experiment was performed.

EXAMPLE 2

To several 200 ml batches of 60° Brix solutions of refined sugar were added 150 ppm of hydrogen peroxide. The samples were heated to various temperatures between 65° and 100° C. To each of the samples were added 10-30 ppm of Takamine Catalase-L and observations on appearance made on the syrups 30-60 seconds after the appearance of the first noticeable bubbles. The degree of creamy appearance is indicative of the expected quality of flotation. The results of the observations are shown in Table 2. Satisfactory flotation will occur only in the samples described as being "creamy" or "very creamy".

TABLE 2

| Temperature | Catalase Level (v/v) | First Bubbles Appear | Degree of Creaminess |
|---|---|---|---|
| 100° C. | 10 ppm | — | no bubbles |
| 100° C. | 30 ppm | 60 sec. | not creamy |
| 90° C. | 10 ppm | 60 sec. | not creamy |
| 90° C. | 30 ppm | 60 sec. | not creamy |
| 80° C. | 10 ppm | 60 sec. | not creamy |
| 80° C. | 30 ppm | 40 sec. | slightly creamy |
| 75° C. | 10 ppm | 60 sec. | not creamy |
| 75° C. | 15 ppm | 60 sec. | not creamy |
| 75° C. | 20 ppm | 45 sec. | slightly creamy |
| 75° C. | 30 ppm | 30 sec. | creamy |
| 72° C. | 10 ppm | 50 sec. | slightly creamy |
| 72° C. | 15 ppm | 30 sec. | very creamy |
| 72° C. | 20 ppm | 20 sec. | very creamy |
| 65° C. | 10 ppm | 45 sec. | slightly creamy |
| 65° C. | 15 ppm | 30 sec. | very creamy |
| 18° C. | 10 ppm | 30 sec. | very creamy |

As would be expected, the higher the temperature of the syrup the more enzyme inactivation takes place. At temperatures above about 75° C., even 30 ppm of the enzyme are inactivated rapidly enough that the necessary degree of creaminess does not appear. At 72° C. and 65° C., 15 ppm of the enzyme suffice to give enough creaminess for flotation. Sufficient creaminess for flotation readily appears at temperatures lower than about 65° C. However, the reaction between phosphoric acid and lime to form an insoluble floc is then not complete, and soluble calcium phosphate species remain in solution and may remain in the sugar syrup after filtration. Thus, syrup temperatures between 65° C. and 72° C. are suitable for the addition of catalase when using a calcium phosphate floc.

In order to determine the effects of enzyme reaction time and stirring time after addition of polyelectrolyte on the quality of flotation, the following experiment was performed.

EXAMPLE 3

A seven-liter batch of 60° Brix syrup was prepared from unrefined sugar and heated to 70° C. To the batch were added 500 ppm of hydrogen peroxide, 0.09% phosphoric acid, 0.1% of lime and a primary was floc allowed to form. The batch was divided into seven portions, and these were treated as follows:

Portion 1. To this portion were added simultaneously eight ppm of polyelectrolyte and eight ppm of catalase. The mixture was stirred for 60 seconds and flotation allowed to take place. After 20 minutes a loose scum, 175 ml in volume, had accumulated at the top of the beaker. A slight amount of the floc had not risen and was dispersed throughtout the liquor.

Portion 2. Eight ppm of catalase were added to this portion and, simultaneously, eight ppm of polyelectrolyte were added. Agitation was continued for 120 seconds. Agitation was then ceased and the flotation allowed to take place. After 20 minutes a loose scum, 150 ml in volume, had formed at the top of the beaker. Some floc was seen in the liquor under the scum.

Portion 3. Eight ppm of catalase were added to this portion and stirred gently for 60 seconds. Eight ppm of polyelectrolyte were then added and agitation continued for another 60 seconds. Agitation was then ceased and the flotation allowed to take place. In 20 minutes a firm scum, 115 ml in volume, had formed at the top of the beaker. No floc particles were seen in the liquor under the scum.

Portion 4. To this portion eight ppm of catalase were added and stirring continued for 60 seconds. After the 60 seconds eight ppm of polyelectrolyte were added and stirring continued for 120 seconds. The floc was then allowed to rise. After 20 minutes a loose scum, 175 ml in volume, had accumulated at the top of the beaker. Some floc was suspended in the liquor under the scum.

Portion 5. Eight ppm of catalase were added to this portion and stirring continued for 60 seconds. After the 60 seconds eight ppm of polyelectrolyte were added and stirring continued for 180 seconds. The floc was then allowed to rise. After 20 minutes a loose scum, 225 ml in volume, had accumulated at the top of the beaker, with much floc suspended in the syrup.

Portion 6. To this portion eight ppm of catalase were added and stirring continued for 120 seconds. After the 120 seconds eight ppm of polyelectrolyte were added and stirring continued for 60 seconds. The floc was then allowed to rise. After 20 minutes a loose scum, 175 ml in volume, had accumulated at the top of the beaker, with a slight amount of floc visible in the syrup.

Portion 7. To this portion eight ppm of catalase were added and stirring continued for 180 seconds. After the 180 seconds eight ppm of polyelectrolyte were added and stirring continued for 60 seconds. The floc was then allowed to rise. After 20 minutes a loose scum, 200 ml in volume, had accumulated at the top of the beaker, with a slight amount of floc visible in the syrup.

Table 3 summarizes the quality of the flotations taking place under the seven timing combinations of Example 3.

TABLE 3

| Addition of Polyelectrolyte (seconds after addition of catalase) | Stirring Time (seconds after addition of polyelectrolyte) | Quality of Flotation (after 20 min.) | |
|---|---|---|---|
| | | Suspended Floc | Scum Volume (ml) |
| 0 | 60 | slight | 175 |
| 0 | 120 | some | 150 |
| 60 | 60 | none | 115 |
| 60 | 120 | some | 175 |
| 60 | 180 | much | 225 |
| 120 | 60 | slight | 175 |
| 180 | 60 | slight | 200 |

These results show that although each time interval, above, may last up to 180 seconds, it is preferable that the enzyme be allowed to act for a period of not more than about one minute before adding the polyelectrolyte, and it is also preferred that stirring be continued for not longer than about one minute after addition of the polyelectrolyte in order to obtain a satisfactory flotation.

In order to show the difference in removal of color between flotation with oxygen bubbles and flotation with air bubbles, the following experiment was conducted.

EXAMPLE 4

A six-liter batch of 60° Brix syrup was made from semi-refined sugar having 650 RBU's. The batch was heated to 70° C., and 0.09% phosphoric acid was added. The pH of the batch was 3.8. The batch was then divided into 6 one-liter portions. To two of the portions was added 0.1% carbon, to another two was added 0.05% carbon, and to the last two, no carbon was added. To one each of the samples with 0.1%, 0.05%, and 0% carbon were added 500 ppm of hydrogen peroxide. The six samples were held at 70° C. for 20 minutes with stirring, after which they were all adjusted to pH 6.3 by the addition of 0.1% lime (based on weight of sugar) and placed in separatory funnels. The three samples containing no hydrogen peroxide were shaken vigorously until very creamy in appearance, and 15 ppm of polyelectrolyte were added anu mixed by swirling. The floc was then allowed to rise. To the other three samples containing hydrogen peroxide were added 10 ppm of Takamine Catalase-L, and when the gas bubble formation was at its peak after approximately 60 seconds, 15 ppm of polyelectrolyte was added and mixed by swirling. When completely in solution, i.e. after about 60 seconds, swirling was stopped and the floc allowed to flotate. Samples of the clarified syrup were taken and filtered with filter aid.

Spectrophotometric readings of the syrup (diluted to 30° Brix) were then taken at 420 and 720 nm, and RBU's calculated.

The results of Example 4 are shown in Table 4.

TABLE 4

| | Reference Base Units (RBU's) | |
|---|---|---|
| | Air Flotation | Oxygen Flotation |
| No Treatment | 650 | 650 |
| No Carbon | 273 | 208 |
| 0.05% Carbon | 151 | 120 |
| 0.10% Carbon | 123 | 81 |

None of the treated samples had any molasses flavor or odor. In addition, however, the data in the table show that more color was removed by the floc flotation involving oxygen generated from hydrogen peroxide and catalase than was removed in the corresponding samples treated by floc flotation involving air.

In order to demonstrate that the peroxide/catalase flotation process conducted on a laboratory scale in the previous Examples may be carried out on a commercial scale, the following experiment was conducted.

EXAMPLE 5

To 500 liters of 60° Brix unrefined sugar syrup in a jacketed vessel with gentle overhead agitation at 68° C. were added 0.09% phosphoric acid and 0.1% activated carbon. Hydrogen peroxide was then added at a level of 500 ppm. In about 20 minutes 0.1% pure lime was added to form a primary calcium phosphate floc with the phosphoric acid. In about 5 minutes, after the calcium phosphate floc had fully formed, eight ppm of catalase were added. The syrup was agitated for 60 seconds, and then immediately 15 ppm of polyelectrolyte were added. Agitation was continued for another 60 seconds and then stopped. The floc immediately started to float to the surface of the syrup to form a compact scum.

After 15 minutes the clear syrup was pumped from the bottom of the tank to another vessel until only the scum was left in the tank. To the 54 kg of scum, or about 8.4% of the original total syrup weight, were added 257 liters of 65° C. water with agitation. The resulting diluted scum syrup had 10.5° Brix. To this syrup were added 375 ppm $H_2O_2$ and 6 ppm catalase. Agitation was continued for 60 seconds, after which time 70 ppm of polyelectrolyte were added to the syrup and agitation continued for another 45 seconds. After stopping the agitation, the floc flotated rapidly to form a scum on the surface of the syrup. After about 15 minutes 290 kg of the clarified, 10.5° Brix syrup were collected from beneath the scum, leaving a scum which weighed 19.5 kg and contained 0.53% of the original sugar. This 10.5° Brix syrup may be recycled for use to dissolve sufficient impure sugar to form a 60° Brix impure sugar syrup for a subsequent purification operation. The "exhausted" scum was discarded.

Samples from the process were analyzed spectrophotometrically at 30° Brix. The values are shown in Table 5.

TABLE 5

| | Spectrophotometric Values | | |
|---|---|---|---|
| | $A_{420}$ | $A_{720}$ | RBU |
| Untreated Sugar (Unfiltered) | .258 | .037 | 530 |
| After Flotation Only | .019 | .000 | 54 |
| After Flotation and Filtration | .016 | .000 | 42 |

These data show that even before the polishing filtration the syrup was free of turbidity and had almost no color. No molasses odor or flavor was detected in the treated syrup.

In order to show that an aluminum hydroxide floc may be conveniently flotated at room temperature in a low Brix syrup, the following experiment was conducted.

EXAMPLE 6

To 338 l of 13° Brix crude sugar at 18° C. in a vessel equipped with a side agitator were added 1.60% aluminum sulfate [$Al_2(SO_4)_3 \cdot 18H_2O$] followed by addition of 0.5% lime. In about five minutes hydrogen peroxide was added at a level of 50 ppm. After the peroxide was dispersed, 10 ppm of catalase were added. The syrup was agitated for 60 seconds, and then immediately 42 ppm of Separan AP30, a polyacrylamide polyelectrolyte manufactured by Dow Chemicals, Inc., were mixed into the syrup for 30 seconds. When the agitation was stopped, the floc immediately started to rise to the surface to form a compact scum.

After 15 minutes the clear syrup was pumped from the bottom of the tank to another vessel until only the scum was left in the tank. The scum weighed 22.7 kg and had a sugar concentration of 13° Brix, and thus, contained 6.4% of the sugar. The scum was discarded, but (as shown hereinbelow in Example 7) the scum may be further treated to recover the sugar entrapped therein.

Spectrophotometric readings of the samples from the process were taken at 720 and 420 nm at 13° Brix. The results are shown in Table 6.

TABLE 6

| | Spectrophotometric Values | | |
|---|---|---|---|
| | $A_{420}$ | $A_{720}$ | RBU |
| Untreated Sugar (Unfiltered) | .519 | .133 | 1766 |
| After Flotation Only | .041 | .002 | 286 |

TABLE 6-continued

| | Spectrophotometric Values | | |
|---|---|---|---|
| | $A_{420}$ | $A_{720}$ | RBU |
| After Flotation and Filtration | .035 | .000 | 272 |

The following experiment demonstrates that an aluminum hydroxide floc may be conveniently flotated with peroxide-catalase gasification in 27.3 Brix syrups at room temperature, although at a higher sugar loss than when the syrup Brix is lower. However, the experiment also shows that most of the sugar which would be lost by virtue of its retention in the scum can be recovered if the sugar in the scum is extracted with water and the resulting low Brix syrup is purified according to the present invention.

EXAMPLE 7

To a 345 liter batch of crude sugar syrup at 27.3° Brix at 18° C. were added 1.16% aluminum sulfate [$Al_2(SO_4)_3 \cdot 18H_2O$] followed by addition of 0.35% lime. In about five minutes hydrogen peroxide was added at a level of 50 ppm. After the peroxide was dispersed, 10 ppm of catalase were added. The syrup was agitated for 60 seconds, and immediately 35 ppm of Separan AP30 (a polyacrylamide polyelectrolyte manufactured under that trademark by Dow Chemicals, Inc.) were mixed into the syrup for 30 seconds. When the agitation was stopped, the floc immediately started to rise to the surface to form a compact scum.

After 15 minutes the clear syrup was pumped from the bottom of the tank to another vessel until only the scum was left in the tank. The scum weighed 52 kg and had a sugar concentration of 27.3° Brix. Thus, it contained 13% of the sugar present in the original syrup. Spectrophotometric readings of samples from the process were taken at 27.3° Brix at 720 nm and 420 nm. The results are shown in Table 7.

TABLE 7

| | Spectrophotometric Values | | |
|---|---|---|---|
| | $A_{420}$ | $A_{720}$ | RBU |
| Untreated Sugar (Unfiltered) | 1.029 | 0.260 | 1678 |
| After Flotation Only | 0.103 | 0.003 | 319 |
| After Flotation and Filtration | 0.096 | 0.000 | 315 |

To the scum remaining after the treated syrup was removed were added 277 liters of 18° C. water. Agitation was started, and 50 ppm $H_2O_2$ were added followed by 10 ppm of Catalase-L. In 60 seconds 100 ppm of Separan AP30 were mixed into the syrup for 30 seconds. When the agitation was stopped, the floc immediately rose to the surface to form a compact scum.

After 5 to 10 minutes the clear dilute syrup was pumped to another vessel to be used for preparing another batch of impure sugar syrup. The "exhausted" scum remaining in the tank, containing only 1.5 kg or 1.4% of the initial sugar, was discarded. Examples 6 and 7 demonstrate the utility of peroxide/catalase flotation on a secondary aluminum hydroxide floc. In general such a floc is useful in low temperature flotation purifications on low Brix syrups. It is contemplated that such flotations are useful over a broad range of 50° Brix or less and over a preferred range of 30° Brix or less.

In order to determine whether alternative methods of practicing the present invention were practicable, the following experiment was conducted.

EXAMPLE 8

A 400-liter batch of 60° Brix unrefined sugar syrup was warmed at 65° C. in a jacketed vessel equipped with overhead agitation. A forty liter portion of the syrup was transferred to a smaller jacketed vessel, while the remainder of the 60° Brix syrup was heated to 70° C. Phosphoric acid and activated carbon (0.09% and 0.1% respectively, both based on weight of total sugar in both portions) were added to the large portion of 70° C. syrup, and, after about 15 minutes, 0.1% lime (based on total weight of sugar in both portions) was added in order to form a primary calcium phosphate floc in the large portion.

The 40 liter portion of syrup was maintained at 65° C., and 20 g (500 ppm based on the volume of the 40 liter portion or 50 ppm based on total syrup volume) $H_2O_2$ were added.

After the $H_2O_2$ was dispersed (about one minute), two ml (50 ppm based on the volume of the 40 liter portion or 5 ppm based on total syrup volume) of catalase were added. The syrup was agitated for about 30 seconds and was then immediately pumped into the larger vessel and mixed with the 360 liters of floc-containing syrup.

When all of the $H_2O_2$/catalase-containing syrup had been transferred into the larger tank, 15 ppm (based on weight of total sugar) of Magnifloc 846A were added at once. Agitation was continued for about one minute and then stopped. The floc immediately started to rise toward the surface of the syrup.

After about 20 minutes a firm scum had formed, and the clear syrup was then pumped from the bottom of the tank to another vessel.

The absorbance values of samples of the clarified syrup were determined at 30° Brix on a spectrophotometer. The values are shown in Table 8.

TABLE 8

| | Spectrophotometric Values | | |
|---|---|---|---|
| | $A_{420}$ | $A_{720}$ | RBU |
| Untreated Sugar (Unfiltered) | 0.983 | .185 | 1814 |
| After Flotation Only | 0.177 | .001 | 518 |
| After Flotation and Filtration | 0.171 | .000 | 506 |

The data show that the color of untreated, unfiltered syrup was reduced by nearly 90% after treatment and filtration. In addition, the treated samples had no detectable molasses flavor or odor.

The procedure employed in Example 8 results in small but significant cost savings. Thus, whereas the flotation of 400 liters of syrup in a full-batch flotation operation would use about 200 g of hydrogen peroxide and about 3.2 ml of catalase, the procedure of Example 8 used only 20 g of hydrogen peroxide and two ml of catalase to achieve virtually the same degree of aeration. Thus the procedure of Example 8 reduces the cost of the oxygen flotation of the present invention.

DISCUSSION OF THE INVENTION

The preceeding examples disclose several embodiments of the invention as it relates to the floc flotation purification of impure sugar syrups; i.e. the process of utilizing a hydrogen peroxide/catalase couple to generate oxygen gas bubbles in combination with utilizing a suitable polyelectrolyte to form a secondary floc such that the secondary floc captures sufficient oxygen gas bubbles to cause it to float. The discussion which follows deals first with the use of the invention in high (40°-65°) Brix syrups, second with its use in low (less than 40°) Brix syrups, third with an alternative method of using the invention in either high or low Brix syrups, and fourth with a generalized apparatus which may be utilized to perform the process.

HIGH BRIX SYRUP PURIFICATION

In accordance with the invention, 40°-65° Brix, preferably about 60° Brix, syrups made from unrefined sugar are treated in the following way. First, the temperature of the syrup is adjusted to about 60°-72° C., preferably about 68°-70° C. Next, sufficient hydrogen peroxide is added to the syrup (conveniently as a 10% aqueous solution) to give the syrup a concentration of not less than about 25 parts per million, preferably about 250 ppm, (based on volume of syrup). While the hydrogen peroxide may be added simultaneously with the catalase at a later stage, it is preferred that the hydrogen peroxide be allowed to remain in contact with the sugar for a period of time in order to achieve maximum decolorization. Next, an aqueous mixture of a phosphate ion source, preferably phosphoric acid, and carbon is added. The amounts and ratios of phosphoric acid and carbon used depend upon the level of impurities in the sugar. Typically, between about 0.03 and about 0.20% of phosphoric acid (based on weight of sugar) most commonly about 0.1%, and 0.05 to 0.2% carbon, typically about 0.1% (based on weight of sugar) are used. The mixture of sugar, hydrogen peroxide, phosphoric acid, and carbon is agitated at about 70° C. for a short period of time, usually about 15 minutes, to achieve uniform distribution and some decolorization. At the end of the holding period between about 0.03 and about 0.20%, typically about 0.1%, of lime is stirred into the sugar syrup causing the formation of a calcium phosphate floc and raising the pH of the resulting syrup to approximately between about 5.5 and about 8, preferably 6.3-6.5, depending on the pH of the original mill sugar.

When the floc is fully formed, not less than about two, and preferably about 2-25, ppm (based on volume of syrup) of a standardized catalase preparation, such as that manufactured by Miles Laboratories under the trademark of Takamine Catalase-L (which contains 100 Keil Units per ml) is added, conveniently in a dilution of about 1:200. A Keil Unit is defined as that quantity of enzyme which will decompose one gram 100% hydrogen peroxide in 10 minutes at 25° C. Other catalase preparations having equivalent catalase activity may, of course, be utilized in place of Takamine Catalase-L. While Miles Laboratories' Takamine Catalase-L has been used throughout the Examples, those skilled in the art will readily recognize that any catalase preparation would function adequately in the present invention so long as it is dispersible, shows sufficient activity to cause rapid peroxide degradation and causes no undesirable side reactions. It is critical to form the oxygen bubbles rapidly so that the syrup will be quickly saturated with bubbles. If the bubbles are formed slowly, i.e., over a period of several minutes, most will dissipate at the surface of the syrup, and the syrup will not be sufficiently saturated with bubbles to give good flotation. The amount of enzyme needed to form enough bubbles for the flotation depends to a large degree on the amount of hydrogen peroxide in the mixture. The more hydrogen peroxide is present, the less enzyme is needed. It has been found that about 250 ppm of hydrogen peroxide and about ten ppm of Takamine Catalase-L (Miles) (both based on volume of syrup) give excellent flotation. However, even excessive use of hydrogen peroxide would nonetheless require at least two ppm of catalase, and conversely even excessive levels of catalase would nevertheless require at least 25 ppm hydrogen peroxide.

The amount of enzyme needed also depends on the temperature. Increasing the temperature increases the rate of bubble formation up to about 72° C., at which point further increases in temperature inactivate the enzyme so rapidly that insufficient bubble formation takes place unless large quantities of enzyme are present. The minimum temperature at which the process may be beneficially practiced with a phosphate floc is approximately 60° C., which is approximately the minimum temperature at which the various calcium phosphate species will convert substantially into insoluble calcium phosphate. If the temperature is lower and this conversion does not take place, soluble calcium phosphates will remain in the syrup even after filtration unless the syrup is subsequently heated before filtration, in which case the insoluble calcium phosphate floc will form and interfere with filtration. Thus, it has been found that temperatures between 60° and 72° C., preferably 68°-70° C., are suitable for phosphate flocs. Under the preferred conditions, bubble formation in the syrup is at its peak about 60 seconds after adding the catalase. With bubble formation at, or near, its peak, and while the syrup is still being stirred, a secondary floc is formed from the primary calcium phosphate floc by the addition of about 8-15 ppm (based on weight of sugar) of a polyelectrolyte, such as Magnifloc 846A, conveniently in a 0.1% aqueous solution. At this dilution it takes approximately 60 seconds to disperse the polyelectrolyte evenly throughout the syrup. In each of the preceeding Examples involving primary phosphate flocs, American Cyanamid's trademarked polyacrylamide polyelectrolyte, Magnifloc 846A, was used to form the secondary floc. The choice of this particular polyelectrolyte was made on the basis of experiments which measured both flotation time and final floc volume for a number of Magnifloc polyelectrolytes at various usage levels. The findings indicated that both test parameters were optimized using Magnifloc 846A. The selection of this particular polyelectrolyte, while indicating its preferability among those tested, is not meant, and should not be interpreted, to limit the breadth of the instant invention to a single polyelectrolyte. The results of the comparison tests referred to above showed that both of the other polyelectrolytes tested, i.e. Magnifloc 845A and 847A functioned adequately at equal usage levels. Moreover, the formation of secondary flocs in flotation processes is well known to those skilled in the art to proceed with a variety of polyelectrolytes. Thus, while some routine experimentation may be necessary to determine whether a particular polyelectrolyte will function in the process of the present invention, it is believed that the present invention is broadly useful and functional with any polyelectrolyte which is capable of forming a flotatable secondary phosphate floc.

Since flotation in the phosphate floc embodiment of the present invention depends on bubble capture and retention by the secondary floc, it is necessary that the agitation used to disperse the polyelectrolyte be sufficiently non-turbulent to avoid breaking up the floc and allowing the oxygen bubbles to escape. Thus an agitator with a vertical shaft (overhead agitation) is preferred. If, for example, an agitator on a horizontal shaft (side agitation) is used in such a way as to induce significant turbulence in the syrup, the secondary phosphate floc may be broken up, allowing the oxygen bubbles to escape thereby making satisfactory flotation impossible. Thus, although either overhead agitation or side agitation may be used, it is critical that the agitation be substantially non-turbulent in order that the secondary floc will not be broken up.

As soon as the polyelectrolyte is completely dispersed, the agitation is stopped. Large aggregates of secondary floc begin to form in a few seconds and at once begin to rise. In approximately ten minutes the floc has formed a compact scum at the surface of the syrup. The scum may comprise, depending upon the amounts of chemicals added, about 5-10% of the total volume of the syrup, and may contain about 4-8% of the total sugar. The clarified liquor under the scum is greatly reduced in color and has no visible turbidity. However, when carbon is used, a small amount of fine carbon particles are held in suspension. The liquor is then separated from the scum and polished by filtration through a filter press. If desired, very small amounts of a filter aid, such as Hyflo SuperCel, and/or activated carbon may be added to the liquor before filtration.

In order to maximize the yield of sugar from the phosphate floc process, the scum may, if desired, be mixed with approximately the amount of water needed for the next batch. The temperature of the resulting dilute syrup is maintained at not greater than 72° C. About 25 or more ppm hydrogen peroxide (based on volume of dilute syrup), preferably about 50 ppm, and about 5-15 ppm (based on volume of dilute syrup) of Catalase-L are added. About 60 seconds after adding the catalase, about 10 ppm (based on weight of sugar) of polyelectrolyte are added. After about 60 seconds, to allow proper dispersion of the ingredients, agitation is stopped and the floc allowed to rise. In the dilute syrup the floc rises very quickly and forms a scum at the surface of the liquid. The scum may comprise 5-10% of the total volume of the dilute syrup, depending upon the amount of floc chemicals previously used in the flotation of the high Brix syrup, and contains perhaps 4-8% of the sugar in the dilute syrup together with the oxygen bubbles. The clarified dilute syrup is then drawn into another tank, and enough impure sugar added to make a new batch of high Brix syrup for treatment with the process of the invention.

LOW BRIX SYRUP PURIFICATION

In addition to its use for the purification of high Brix (40°-70° Brix) impure sugar syrups, the novel process of utilizing oxygen bubbles for floc flotation may also be applied to the purification of low Brix (less than 40° Brix, and preferably less than 30° Brix) impure sugar syrups. As shown in Examples 6 and 7, low Brix syrups may be treated with a primary floc-forming chemical couple comprising an aluminum ion source and lime, rather than the phosphate-lime chemical couple used for high Brix syrups. For low Brix syrups, this couple has the advantage over the phosphate couple of substantially complete primary floc formation at, or even significantly below, room temperature, thus allowing a far broader temperature range than available with the phosphate-lime couple.

In accordance with this embodiment of the process using aluminum hydroxide primary floc, an impure sugar syrup of less than 40° Brix, preferably less than 30° Brix, is first treated with an aluminum ion source and lime in order to form the primary floc. The final level of addition of both members of the chemical couple, as well as the ratio between the two, is dependent on the level of impurities in the syrup. Typically, between about 0.8 and 3.0% of aluminum sulfate [$Al_2(SO_4)_3 \cdot 18H_2O$] (or equivalent levels of an alternative aluminum ion source), preferably between about 1 and 2%; and between about 0.2% and 1.0% of lime (preferably between about 0.3-0.6%) are added. Optionally 0.05 to 0.2% of activated carbon may be added for additional decolorization.

After the formation of the primary floc, hydrogen peroxide is added as a 5-20% solution, conveniently about a 10% solution, in an amount sufficient to give the syrup a concentration of not less than about 25 ppm, preferably about 50 ppm. As with the phosphate floc process for high Brix syrups described above, the order of addition of the aluminum ion source, the lime and the hydrogen peroxide is not critical.

Subsequent to the peroxide addition, sufficient catalase is mixed into the syrup to cause rapid evolution of oxygen gas bubbles. Typically, 2-25 ppm, preferably about ten ppm, of Miles Laboratories Catalase-L is added and thoroughly dispersed to allow uniform bubble generation. While not critical, the Catalase-L concentration in the added solution should be about 1:200 (or an equivalent dilution of an alternative form of catalase) since the volume of the catalase solution should be sufficiently large to be uniformly distributable throughout the syrup in a minimum time.

Not more than about 180 seconds, preferably not more than 120 seconds, and optimally not more than about 60 seconds following the addition of the catalase, about 20-50 ppm, and preferably 30-40 ppm of a polyelectrolyte, such as Dow Chemical Company's Separan AP30, is uniformly distributed throughout the bubbling syrup in order to form a secondary floc containing the primary aluminum hydroxide floc, residual impurities, activated carbon, and oxygen bubbles. As distinguished from the case of secondary phosphate floc flotation in high Brix syrups discussed above, it is not as critical for low Brix syrups that this uniform distribution of polyelectrolyte be accomplished by substantially non-turbulent means since, in low Brix syrups the secondary aluminum hydroxide floc less readily loses the captured oxygen bubbles which give it its buoyancy.

The agitation may be continued for up to 180 seconds, preferably 120 seconds and optimally up to 60 seconds in order to attain uniform distribution. The agitation is then discontinued, and the floc allowed to rise to form a scum floating on the purified low Brix syrup. The syrup is then withdrawn from the purification vessel and further treated to recover the sugar therefrom. The scum may either be discarded, or optionally further processed to recover the sugar which it contains. In order to accomplish the latter option, the scum is mixed in approximately the amount of water which will be needed to make up the next batch of low Brix syrup for purification, agitated to extract the sugar from the scum, treated with effective amounts of hydrogen peroxide and catalase, and treated with an additional amount of polyelectrolyte to form a second secondary floc which is allowed to rise leaving a dilute syrup which may be drawn off and utilized to dissolve additional impure sugar to form a low Brix syrup which is purified by the process.

As was the case with the phosphate floc process for high Brix syrups, the choice of polyelectrolyte in the low Brix process is not critical so long as it is capable of forming a flotatable secondary floc from primary aluminum hydroxide floc. While Dow Chemical Company's Separan AP30 was selected for use in Examples 6 and 7, routine experimentation, well within the knowledge and skill of practitioners of the flotation arts, may show several alternative polyelectrolytes, any one of which may be compatible with, and useful in, the present invention. It is therefore to be understood that the present invention is not to be limited to the use of a particular polyelectrolyte, but rather to encompass the use of any polyelectrolyte which is substantially functionally equivalent to those disclosed in the foregoing Examples.

As is the case of high Brix syrups, the secondary floc formed in low Brix syrup purification will contain a small percentage of the sugar present in the original, low Brix syrup. This secondary floc may be treated in a fashion analogous to that discussed above for phosphate secondary flocs in order to recover this sugar. However, since the sugar concentration in the original low Brix syrup is relatively low, the total weight of sugar contained in the secondary floc will be relatively small and its recovery, therefore, may not be economically justified. Nevertheless, such a recovery operation is considered to be an optional step in the purification of low Brix syrups and to comprise a portion of the instant invention.

ALTERNATIVE METHOD OF PRACTICING THE INVENTION

In the preceeding discussion, the utility of the present invention for purifying high Brix syrups (in conjunction with a calcium phosphate secondary floc) and low Brix syrups (in conjunction with an aluminum hydroxide secondary floc) is disclosed. In general, both of these embodiments call for the practioner to dissolve raw sugar in sufficient water to yield a syrup of the desired Brix and to treat the entire volume of syrup with hydrogen peroxide, catalase and polyelectrolyte in order to obtain a purified syrup. However, as shown in Example 8, there is an alternative method of practicing the invention which allows the practioner to utilize lower amounts of hydrogen peroxide and catalase yet nevertheless obtain a substantially equivalent degree of sugar purification. Although Example 8 discloses the use of this alternative embodiment in conjunction with the purification of a high Brix syrup, this alternative method is also useful for purifying a low Brix syrup.

In this alternative method of practicing the invention, the syrup is divided into a large portion containing from about 80% to about 95%, preferably about 90%, of the syrup, and a small portion containing the remainder. The primary floc forming chemical couple (lime/phosphate ion source for a high Brix syrup or lime/aluminum salt for a low Brix syrup) is added to the large portion in an amount precalculated to form sufficient primary floc to purify the total amount of sugar in the syrup, i.e. that amount of sugar in both portions. This in a high Brix syrup, between about 0.03% and about 0.2%, preferably about 0.1%, of lime and between about 0.03% and about 0.2%, preferably about 0.1%, of phosphoric acid are added to the large portion. In a low Brix syrup, between about 0.2% and about 1.0%, preferably between about 0.3% and 0.6%, of lime and between about 0.8% and about 3.0%, preferably between about 1.0% and 2.0%, of aluminum sulfate are added to the large portion.

In the case of high Brix Syrups, the small portion, is treated with sufficient hydrogen peroxide to yield a peroxide concentration of not less than about 25 ppm based on total syrup volume (250 ppm based on the small portion volume in the case where the volume of the small portion is 10% of the total volume), preferably between about 50 and about 100 ppm based on the total syrup volume. Once this hydrogen peroxide has been dispersed throughout the small portion, catalase is added to the small portion and dispersed throughout the small portion quickly, usually in less than about 60 seconds, preferably not more than about 30 seconds. Sufficient catalase is added to yield a catalase concentration of not less than about 3 ppm based on total syrup volume (30 ppm based on the small portion volume in the case where the volume of the small portion is 10% of the total syrup volume), preferably between about 5 ppm and about 20 ppm based on the total syrup volume.

In the case of low Brix syrups, the small portion is treated with sufficient hydrogen peroxide to yield a peroxide concentration of not less than about 25 ppm based on total syrup volume (250 ppm based on the small portion volume in the case where the volume of the small portion is 10% of the total volume), preferably between about 50 ppm and about 100 ppm based on total syrup volume. Also in the case of low Brix syrups, sufficient catalase is added to, and rapidly dispersed in, the small portion to yield a catalase concentration of not less than about 3 ppm based on total syrup volume (30 ppm based on the small portion volume in the case where the volume of the small portion if 10% of the total syrup volume), preferably between about 5 ppm and about 20 ppm based ppm the total syrup volume.

In either the high Brix or the low Brix application, once the catalase has been dispersed and oxygen gas bubble formation has begun, the small portion is rapidly recombined with the large portion, is polyelectrolyte added and secondary floc flotation allowed to occur. Polyelectrolyte is added to the recombined syrup in substantially the same manner and amount as in the conventional practice of the invention, i.e. between about 8 and about 15 ppm in high Brix syrups and between about 20 and 50 ppm, preferably between about 30 and 40 ppm in low Brix syrups.

As in the other embodiments of the present invention, the secondary floc formed during the practice of the alternative embodiment may be dispersed in water and treated with additional amounts of peroxide, catalase and polyelectrolyte to recover the sugar captured by the secondary floc. This recovery may be carried out as previously described, or it may be accomplished using the two-portion alternative embodiment as described above with modifications obvious to those skilled in the art.

By using this alternative method of practicing the invention, it is possible to substantially decrease the amounts of hydrogen peroxide and catalase used to obtain purification without sacrificing the degree of purification obtained. In addition, if one were to use the alternative method to purify a high Brix syrup, the large portion could be heated to a higher temperature resulting in more rapid formation of insoluble calcium phosphate species while the smaller portion could be maintained at a lower temperature in order to minimize thermal inactivation of the catalase. Although heating the large portion substantially in excess of 70° C. may result in inactivation of the catalase upon recombination, the effect of such inactivation may be minimized by allowing oxygen generation to proceed to substantial completion in the small portion prior to recombining the two portions. The selection of the two portion's temperatures and the selection of the time delay prior to recombining may be adjusted by the practitioner to optimize the flotation. Such routine experimentation as may be required to select these dependant variables is considered to be well within the level of skill of practitioners in the art.

APPARATUS FOR PURIFICATION OF SUGAR SYRUPS

The invention will be further described with reference to the schematic representation of a floc-flotation apparatus shown in the accompanying drawing.

Referring to the drawing, process water at a temperature of about 90° C. is pumped through a primary water pipe, 1, into a jacketed primary flotation tank, 2. At the same time, impure crystalline sugar is introduced into the tank through a primary chute, 4, and the resulting syrup continuously agitated by a primary nonturbulent agitator, 3. A 10% solution of hydrogen peroxide is dosed into the sugar solution through a primary chemical inlet pipe, 5, while the sugar is being introduced. When all the sugar is in solution and the temperature is at about 70° C., an aqueous slurry of activated carbon in phosphoric acid is dosed into the syrup through pipe 5. After a holding period of up to about 20 minutes at about 70° C., a 20% slurry of lime is added through pipe 5 to neutralize the acid in the syrup and to form a primary floc. As an alternative to the use of a calcium phosphate floc, a primary aluminum hydroxide floc may be formed by dosing a solution of aluminum sulfate containing slurried activated carbon into the syrup through pipe 5, maintaining the temperature of the resultant slurry at any desired temperature below 72° C., and subsequently adding the slurry of lime through pipe 5. In neither case, i.e. phosphate floc or aluminum hydroxide floc, is the order of addition of the peroxide and chemical couple critical. It is preferred, however, to allow the hydrogen peroxide to remain in the syrup for a short period of time prior to catalase addition in order to achieve a certain amount of decolorization.

When the primary floc is completely formed, catalase solution is dosed into the syrup through pipe 5. About 60 seconds after adding the catalase solution, a solution of the polyelectrolyte is added, also through pipe 5, stirring is continued for about 60 seconds and then stopped. Flotation now proceeds, and in about ten minutes the clarified syrup is ready to be removed from the tank by pumping through a primary pump, 6. Previously, a suspension of carbon and filter aid has been prepared in a mixing tank, 7, and recirculated by a mixing pump, 8, through a filter, 10, to form a precoat. The syrup is now pumped by pump 6 through filter 10, drawing filter aid (and, optionally, carbon) through an injector, 9, and is, in the case of a primary phosphate floc, chilled to less than about 32° C. by passing through a heat exchanger, 11. The syrup then continues through a syrup pipe, 12, into a product storage tank, 13, until all the clarified syrup has been removed from tank 2. To the scum remaining in tank 2 is added a volume of hot water approximately equal to that needed to make up the next batch of syrup while agitating with agitator 3. To this mixture are added hydrogen peroxide and, subsequently, catalase through pipe 5. About 60 seconds after addition of the catalase an appropriate amount of polyelectrolyte is added through pipe 5, and 60 seconds later agitation is stopped and the floc allowed to rise. The floc rises very fast in the dilute syrup, and after approximately five minutes the dilute syrup is pumped by pump 6 into jacketed secondary flotation tank 15. The exhausted scum is discarded. Enough sugar is added to the dilute syrup present in secondary flotation tank 15 via the secondary chute 17, and enough water is added to tank 15 via secondary water pipe 14, to give a batch of syrup of the desired Brix. The chemicals are then added in the same order and amounts as in the first flotation of high Brix syrup through secondary chemical inlet pipe 18, with agitation by secondary agitator 16, and the flotation process is then repeated in tank 15. After clarification of this high Brix syrup, the clarified syrup is pumped by pump 6 from tank 15 into tank 13 through filter 10 and heat exchanger 11 as described above. The scum is diluted, clarified as described above and the exhausted scum discarded. The clarified dilute syrup is then pumped via pump 6 into tank 2 to be made into a high Brix syrup and the process repeated.

From the foregoing description, it will be apparent that changes in the process, steps or order of steps as described herein may occur to persons skilled in the art without departing from the scope and spirit of the invention. Accordingly, the foregoing description is considered to be only exemplary of the invention as defined in the appended claims.

What is claimed is:

1. A process for the purification of an impure sugar syrup comprising:

a. maintaining said syrup at a temperature not greater than about 72° C. and not less than that at which formation of a primary floc may proceed to substantial completion;

b. combining said syrup with not less than about 25 ppm of hydrogen peroxide by volume of syrup, and an amount of a primary-floc-forming chemical couple sufficient to form a primary floc in said hydrogen peroxide containing syrup, said primary floc being formed in an amount sufficient to capture a substantial portion of the impurities present in said syrup;

c. mixing into said syrup an amount of catalase sufficient to cause rapid decomposition of said hydrogen peroxide with resultant rapid generation of oxygen bubbles;

d. dispersing throughout said syrup an amount of a polyelectrolyte sufficient to form a secondary floc having entrapped therein sufficient quantities of said oxygen bubbles to cause flotation, said dispersing being done by agitation such that a sufficient amount of said bubbles will be retained by said secondary floc to cause flotation, said dispersing being begun not more than about 180 seconds following said mixing;

e. discontinuing said agitation not more than about 180 seconds following the commencement of said dispersing;

f. allowing the flotation of said secondary floc thereby leaving a substantially purified sugar syrup; and g. separating said purified sugar syrup from said secondary floc.

2. The process as set forth in claim 1 wherein said discontinuing is accomplished not longer than about 120 seconds following the commencement of said dispersing.

3. The process as set forth in claim 1 wherein said dispersing is done not more than about 120 seconds following said mixing.

4. The process as set forth in claim 1 wherein said discontinuing is accomplished not more than about 60 seconds following the commencement of said dispersing.

5. The process as set forth in claim 1 wherein dispersing is done not more than about 60 seconds following said mixing.

6. The process as set forth in claim 1 wherein said mixing and said dispersing are accomplished simultaneously.

7. The process as set forth in claim 1 wherein said combining comprises a. adding said hydrogen peroxide and said primary member of said chemical couple to said syrup; and b. subsequently adding said secondary member of said chemical couple to said syrup.

8. The process as set forth in claim 1 wherein said combining comprises a. adding said chemical couple to said syrup; and b. Subsequently adding said hydrogen peroxide to said syrup.

9. The process as set forth in claim 7 wherein said sugar syrup is not less than about 40° Brix, wherein said first member of said chemical couple comprises a phosphate ion source and said second member comprises lime and wherein said temperature is from about 60° C. to about 72° C.

10. The process as set forth in claim 9 additionally comprising:

a. slurry said secondary floc of said sugar in sufficient water to form a dilute sugar syrup containing secondary floc particles, said dilute syrup having a temperature of not greater than about 72° C.;

b. treating said dilute sugar syrup with not less than about 25 ppm hydrogen peroxide by volume of said dilute syrup and not less than about two ppm of catalase by volume of said dilute syrup such that rapid generation of oxygen bubbles is caused to occur;

c. uniformly distributing said hydrogen peroxide and said catalase throughout said dilute syrup;

d. introducing into said dilute syrup with agitation sufficient polyelectrolyte to agglomerate said secondary floc particles and to capture a sufficient amount of said oxygen bubbles to cause flotation of said agglomeration, said introducing begun not more than 180 seconds following said uniformly distributing;

e. ceasing said agitation not more than 180 seconds following said introducing:

f. allowing the flotation of said agglomeration to form a scum and to leave a substantially purified dilute syrup; and g. removing said purified dilute syrup from said scum.

11. The process as set forth in claim 8 wherein said sugar syrup is not greater than about 40° Brix, wherein said temperature is from about 0° C. to about 72° C., and wherein said primary member of said chemical couple comprises an aluminum ion source and said secondary member comprises lime.

12. A process for the purification of impure sugar syrups of not less than 40° Brix comprising:

a. maintaining said syrup at a temperature between about 60° C. and about 72° C.;
b. combining said sugar syrup with not less than about 25 ppm hydrogen peroxide by volume of syrup, a phosphate ion source and lime, said phosphate ion source and said lime being provided respectively in amounts sufficient to form an amount of a primary calcium phosphate floc sufficient to capture a substantial portion of the impurities present in said syrup;
c. mixing into said syrup an amount of catalase sufficient to cause rapid decomposition of said hydrogen peroxide with resultant rapid generation of oxygen bubbles;
d. dispersing throughout said syrup an amount of a polyelectrolyte sufficient to form a secondary calcium phosphate floc, said dispersing being done by substantially non-turbulent agitation and after a time interval following said mixing;
e. discontinuing said non-turbulent agitation not more than about 180 seconds following the commencement of said dispersing:
f. allowing the flotation of said secondary floc containing said impurities and a portion of the sugar from said syrup to leave a substantially purified sugar syrup; and
g. separating said purified sugar syrup from said secondary floc.

13. The process as set forth in claim 12 wherein said phosphate ion source is phosphoric acid and wherein said phosphoric acid is added in an amount between about 0.03% and about 0.20% based on the weight of sugar in said impure sugar syrup and said lime is added in an amount between about 0.03% and about 0.2% based on the weight of said sugar sufficient to raise the pH of said syrup to between about 5.5 and about 8.

14. The process as set forth in claim 13 wherein said combining comprises a. adding said hydrogen peroxide and said phosphoric acid to said impure sugar syrup; and
b. subsequently adding said lime to said impure sugar syrup.

15. The process as set forth in claim 14 wherein said dispersing is commenced not more than about 120 seconds following said mixing and wherein said discontinuing is accomplished not more than about 120 seconds following the commencement of said dispersing.

16. The process as set forth in claim 15 wherein said dispersing is commenced not more than about 60 seconds following said mixing and wherein said discontinuing is accomplished not more than about 60 seconds following the commencement of said dispersing.

17. The process as set forth in claim 16 wherein said impure sugar syrup is about 60° Brix, wherein said polyelectrolyte is a polyacrylamide present in an amount between about eight ppm and about fifteen ppm by weight of sugar and wherein said catalase is a beef liver catalase present in an amount not less than two ppm by volume of syrup.

18. The process as set forth in claim 17 additionally comprising introducing an effective amount of activated carbon into said syrup prior to said mixing and removing said carbon from said purified sugar syrup.

19. The process as set forth in claim 17 wherein said lime and said phosphoric acid are added to said syrup in amounts sufficient to yield an initial concentration for each of about 0.1% based on the weight of sugar, and wherein said hydrogen peroxide and said catalase are added in amounts sufficient to yield initial concentrations of about 250 ppm and between about 2 and 25 ppm respectively based on the volume of syrup.

20. The process as set forth in claim 17 additionally comprising:

a. slurrying said secondary floc containing said portion of said sugar in sufficient water to form a dilute sugar syrup containing secondary floc particles, said dilute syrup having a temperature of not greater than about 72° C.;
b. treating said dilute sugar syrup with not less than about 25 ppm hydrogen peroxide by volume of said dilute syrup and not less than about two ppm of catalase by volume of said dilute syrup such that rapid generation of oxygen bubbles is caused to occur;
c. uniformly distributing said hydrogen peroxide and said catalase throughout said dilute syrup;
d. introducing into said dilute syrup with agitation sufficient polyacrylamide to agglomerate said secondary floc particles and to capture a sufficient amount of said oxygen bubbles to cause the flotation of said agglomeration, said introducing begun not more than 180 seconds following said uniformly distributing;
e. ceasing said agitation not more than 180 seconds following said introducing;
f. causing the flotation of said agglomeration to form a scum and to leave a substantially purified dilute syrup; and
g. separating said scum from said purified syrup.

21. The process as set forth in claim 20 wherein the hydrogen peroxide, said catalase and said polyacrylamide are each added to said syrup in amounts sufficient to yield initial concentrations for each of about 50 ppm (based on volume of syrup), between about 5 and about 15 ppm (based on volume of syrup) and about 10 ppm (based on weight of sugar), respectively.

22. The process as set forth in claim 20 wherein said introducing is begun not more than 60 seconds following said uniformly distributing and wherein said ceasing is accomplished not more than 60 seconds following said introducing.

23. A process for the purification of an impure sugar syrup of not less than 40° Brix comprising:

a. maintaining said syrup at a temperature between about 68° and 70° C.;
b. combining said sugar syrup with about 250 ppm of hydrogen peroxide based on volume of said syrup, and about 0.1% each of phosphoric acid and lime, both based on the weight of sugar in said syrup;
c. mixing into said syrup between about 2 and about 25 ppm, based on volume of said syrup, of catalase;
d. not more than about 60 seconds following said mixing, dispersing between about 8 and about 15 ppm by weight of a polyelectrolyte to form a secondary floc, said dispersing being done by substantially nonturbulent agitation for a period of time not greater than 60 seconds;
e. allowing the flotation of said secondary floc containing said impurities and a portion of said sugar to leave a substantially purified sugar syrup;

f. separating said secondary floc from said substantially purified sugar syrup;
g. slurrying said secondary floc containing said portion of said sugar in sufficient water to form a dilute sugar syrup containing secondary floc particles;
h. treating said dilute sugar syrup with about 50 ppm of hydrogen peroxide and between about 5 and 10 ppm of catalase, both based on the volume of said dilute sugar syrup;
i. uniformly distributing said hydrogen peroxide and said catalase throughout said dilute sugar syrup for a period not greater than about 60 seconds;
j. introducing about 10 ppm, based on weight of sugar in said dilute syrup, of a polyelectrolyte into said dilute sugar syrup by agitation to form an agglomerated secondary floc scum;
k. not more than about 60 seconds following said introducing, ceasing said agitation to thereby cause flotation of said scum and to leave a substantially purified dilute sugar syrup;
l. separating said substantially purified dilute sugar syrup from said scum; and
m. utilizing said substantially purified dilute sugar syrup to dissolve sufficient impure sugar to form said impure sugar syrup.

24. The process as set forth in claim 20 additionally comprising discarding said scum and dissolving sufficient impure sugar in said purified dilute syrup to form said impure sugar syrup of not less than about 40° Brix.

25. A process for the purification of impure sugar syrups of not more than about 40° Brix comprising:
a. maintaining said syrup at a temperature not greater than about 72° C. and not less than that at which sugar crystallizes from said syrup;
b. combining said syrup with not less than about 25 ppm hydrogen peroxide, an aluminum ion source and lime, said aluminum ion source and said lime being provided respectively in amounts sufficient to form a volume of a primary aluminum hydroxide floc sufficient to capture a substantial portion of the impurities present in said syrup;
c. mixing into said syrup an amount of catalase sufficient to cause rapid decomposition of said hydrogen peroxide with resultant rapid generation of oxygen bubbles;
d. dispersing throughout said syrup an amount of a polyelectrolyte sufficient to form a secondary floc, said dispersing being done not more than about 180 seconds following said mixing such that a sufficient amount of said oxygen gas bubbles will be entrapped in said secondary floc to cause said secondary floc to cause flotation;
e. discontinuing said agitation not more than about 180 seconds following the commencement of said dispersing;
f. allowing the flotation of said secondary flock, containing said impurities, and a portion of the sugar from said syrup, to thereby leave a substantially purified sugar syrup; and
g. separating said purified sugar syrup from said secondary floc.

26. The process as set forth in claim 25 wherein said aluminum ion source is $Al_2(SO_4)_3.18H_2O$, wherein said aluminum sulfate is added in an amount between about 0.8% and about 3.0% based on the weight of sugar in said impure sugar syrup, and wherein said lime is added in an amount between about 0.2% and about 1.0% by weight of sugar and sufficient to convert substantially all aluminum ion present in said syrup into an aluminum hydroxide floc.

27. The process as set forth in claim 26 wherein said combining comprises
a. adding said aluminum sulfate and said lime to said impure sugar syrup and;
b. subsequently adding said hydrogen peroxide to said impure sugar syrup.

28. The process as set forth in claim 27 wherein said dispersing is commenced not more than about 120 seconds following said mixing and wherein said discontinuing is accomplished not more than about 120 seconds following the commencement of said dispersing.

29. The process as set forth in claim 28 wherein said dispersing is commenced not more than about 60 seconds following said mixing and wherein said discontinuing is accomplished not more than about 60 seconds following the commencement of said dispersing.

30. The process as set forth in claim 29 wherein said impure sugar syrup is not more than about 30° Brix.

31. The process as set forth in claim 17 additionally comprising introducing into said impure sugar syrup prior to said dispersing an amount of activated carbon sufficient to substantially decolorize said impure sugar syrup, and removing said carbon from said purified sugar syrup.

32. The process as set forth in claim 31 wherein the temperature of said impure sugar syrup is not greater than about room temperature.

33. The process as set forth in claim 31 wherein said aluminum sulfate and said lime are added in amounts sufficient to yield an initial concentration of between about 1% and 2% and between about 0.3% and 0.6% respectively, both based on weight of sugar.

34. The process as set forth in claim 31 wherein said polyelectrolyte is a polyacrylamide present in an amount between about 20 and about 50 ppm by weight of sugar and wherein said catalase is a beef liver catalase present in an amount not less than about two ppm by volume of syrup.

35. The process as set forth in claim 34 wherein said polyacrylamide is present in an amount between about 30 and about 40 ppm by weight of sugar.

36. A process for the purification of impure sugar syrups of not more than about 40° Brix comprising:
a. maintaining said syrup at about ambient temperature;
b. combining said syrup with between about 1% and 2% of $Al_2(SO_4)_3.18H_2O$ and between about 0.3% and 0.6% of lime, both based on the weight of sugar in said impure sugar syrup and with about 50 ppm of hydrogen peroxide, based on syrup volume;
c. mixing about 10 ppm of catalase into said syrup;
d. dispersing between about 30 ppm and about 40 ppm of a polyelectrolyte throughout said syrup such that a secondary floc is formed, said dispersing begun not more than about 60 seconds subsequent to said mixing; and
e. discontinuing said dispersing after not more than about 60 seconds to cause flotation of said secondary floc thereby leaving a substantially purified sugar syrup.

37. A process for the purification of an impure sugar syrup containing:
a. dividing said syrup into a large portion and a small portion, said large portion containing between about 80% and about 95% of the volume of the impure sugar syrup;

b. maintaining the temperature of said large portion such that formation of a primary floc will proceed to substantial completion and maintaining the temperature of said small portion at not higher than 72° C.;
c. combining said large portion with an amount of a primary floc-forming chemical couple sufficient to form an amount of primary floc sufficient to capture a substantial portion of the impurities in said large portion;
d. incorporating into said small portion not less than about 250 ppm hydrogen peroxide by volume of said small portion;
e. mixing into said small portion an amount of catalase sufficient to cause rapid decomposition of said hydrogen peroxide with consequent rapid evolution of oxygen bubbles;
f. recombining said small portion with said large portion during said rapid evolution of oxygen bubbles;
g. dispersing throughout said recombined impure sugar syrup an amount of a polyelectrolyte sufficient to form a secondary floc entrapping therein a portion of said oxygen bubbles, said dispersing being done by agitation such that said secondary floc will not be broken up and will not allow said entrapped bubbles to escape, said dispersing being done at a time not more than 180 seconds following said mixing;
h. discontinuing said agitation not more than 180 seconds following the commencement of said dispersing to cause flotation of said secondary floc; and
i. separating said purified sugar syrup from said secondary floc.

38. The process as set forth in claim 37 wherein said dispersing is commenced not more than about 120 seconds after said mixing and wherein said discontinuing is accomplished not more than about 120 seconds following the commencement of said dispersing.

39. The process as set forth in claim 38 wherein said dispersing is commenced not more than about 60 seconds after said mixing and wherein said discontinuing is accomplished not more than about 60 seconds following the commencement of said dispersing.

40. The process as set forth in claim 37 wherein said impure sugar syrup is not less than about 40° Brix and wherein said primary floc-forming chemical couple is a phosphate ion source and lime.

41. The process as set forth in claim 40 wherein said phosphate ion source is phosphoric acid and wherein said lime and said phosphoric acid are added to said large portion in amounts sufficient to yield initial concentrations for each of between about 0.03% and about 0.2% based on the total weight of sugar present in both portions.

42. The process as set forth in claim 41 wherein said lime and said phosphoric acid are added to said large portion in amounts sufficient to yield initial concentrations for each of about 0.1% based on the total weight of sugar present in both portions.

43. The process as set forth in claim 40 wherein said hydrogen peroxide and said catalase are each added to said small portion in amounts sufficient to yield initial concentrations of not less than about 25 ppm and not less than about 3 ppm respectively, both said concentrations based on total volume of both portions.

44. The process as set forth in claim 43 wherein said hydrogen peroxide and said catalase are each added to said small portion in amounts sufficient to yield initial concentrations of between about 50 and about 100 ppm and between about 5 ppm and about 20 ppm, respectively, both of said concentrations based being on total volume of both portions.

45. The process as set forth in claim 40 wherein said polyelectrolyte is a polyacrylamide and wherein said polyacrylamide is added to said recombined syrup in an amount sufficient to yield an initial concentration of between about 8 and about 15 ppm based on total weight of sugar.

46. The process as set forth in claim 40 wherein the temperature of said large portion is maintained at about 70° C. and the temperature of said small portion is maintained at about 65° C.

47. The process as set forth in claim 46 wherein said large portion comprises 90% of the impure sugar syrup.

48. The process as set forth in claim 39 wherein said impure sugar syrup is not more than about 40° Brix and wherein said primary floc-forming chemical coupler is lime and $Al_2(SO_4)_3 \cdot 18H_2O$.

49. The process as set forth in claim 48 wherein said lime and said aluminum sulfate are added to said large portion in amounts sufficient to yield initial concentrations for each of between about 0.2% and about 1.0% and between about 0.8% and about 3.0%, respectively, each based on total weight of sugar present in both portions.

50. The process as set forth in claim 49 wherein said lime and said aluminum sulfate are added to said large portion in amounts sufficient to yield initial concentrations of between about 0.3% and about 0.6% and between about 1.0% and 2.0%, respectively, based on total weight of sugar in both portions.

51. The process as set forth in claim 48 wherein said hydrogen peroxide and said catalase are each added to said small portion in amounts sufficient to yield initial concentrations of not less than about 25 ppm and not less than about 3 ppm, respectively, both based on total volume of syrup in both portions.

52. The process as set forth in claim 51 wherein said hydrogen peroxide and said catalase are each added to said small portion in amounts sufficient to yield initial concentrations of between about 50 ppm and about 100 ppm and between about 5 ppm and about 20 ppm, respectively, both based on total volume of syrup in both portions.

53. The process as set forth in claim 48 wherein said polyelectrolyte is added in amount sufficient to yield an initial concentration of not less than about 25 ppm based on total weight of sugar.

54. The process as set forth in claim 53 wherein the initial concentration of polyelectrolyte is about 50 ppm based on total weight of sugar.

55. A process for the purification of an impure sugar syrup of not less than about 40° Brix comprising:

a. dividing said syrup into a large portion and a small portion;
b. maintaining the temperature of said large portion at not less than about 70° C. and the temperature of said small portion at not greater than about 65° C.;
c. combining said large portion with phosphoric acid and lime
d. incorporating into said small portion between about 500 and 1000 ppm of hydrogen peroxide said concentration being based on the volume of said small portion;

e. mixing into said small portion between about 50 and 200 ppm of catalase, said concentration being based on the volume of said small portion;
f. recombining said small portion with said large portion not more than 30 seconds subsequent to said mixing;
g. substantially non-turbulently dispersing between about 8 and about 15 ppm of a polyelectrolyte throughout said recombined syrup, said concentrations based on total weight of sugar in said syrup and said dispersing done not more than about 60 seconds subsequent to said mixing;
h. discontinuing said substantially non-turbulent dispersing not more than about 60 seconds following its commencement to allow a secondary floc to form;
i. allowing the flotation of said secondary floc thereby leaving a purified sugar syrup;
j. separating said purified sugar syrup from said secondary floc;
k. recovering sugar entrapped in said secondary floc, said sugar recovered in the form of a dilute syrup for use in preparing said impure sugar syrup.

56. A process for the purification of an impure sugar syrup of not greater than 40° Brix comprising:
a. dividing said syrup into a large portion and a small portion;
b. maintaining the temperature of both portions at about ambient temperature;
c. combining said large portion with between about 0.3% and 0.6% lime and between about 1% and about 2% of $Al_2(SO_4)_3 \cdot 18H_2O$, and said percentages based on the total weight of sugar in both portions;
d. incorporating into said small portion between about 500 ppm and 1000 ppm hydrogen peroxide based on the volume of said small portion;
e. mixing into said small portion, between about 50 ppm and 200 ppm of catalase based on the volume of said small portion such that rapid evolution of oxygen bubbles is caused to occur;
f. recombining said small portion with said large portion not more than 30 seconds following said mixing;
g. dispersing throughout said recombined impure sugar syrup between about 30 ppm and about 40 ppm, based on weight of sugar in said recombined syrup, a polyelectrolyte such that a secondary floc is caused to form, said dispersing being commenced not more than 60 seconds following said mixing;
h. discontinuing said dispersing after not more than 60 seconds;
i. allowing the flotation of said secondary floc thereby leaving a substantially purified sugar syrup; and
j. separating said purified sugar syrup from said secondary floc.

57. A process for the purification of impure sugar syrups comprising:
a. adding a primary-floc-forming chemical to said impure sugar syrup in an amount sufficient to form a primary floc and to capture a substantial portion of the impurities present in said syrup;
b. adding hydrogen peroxide to said sugar syrup;
c. dispersing catalase and a polyelectrolyte into said sugar syrup, said catalase being present in an amount sufficient to cause rapid decomposition of said hydrogen peroxide to form oxygen bubbles, said polyelectrolyte being present in an amount sufficient to form a secondary floc having entrapped therein sufficient quantities of said oxygen bubbles to cause flotation of said secondary floc, said dispersing being performed in such a manner that said secondary floc is not broken up;
d. causing the flotation of said secondary floc thereby leaving a substantially pure sugar syrup; and
e. separating said purified sugar syrup from said secondary floc.

58. The process as set forth in claim 57, wherein said dispersing is accomplished by substantially non-turbulent agitation.

59. The process as set forth in claim 57, wherein said hydrogen peroxide is added in an amount of at least 25 ppm by volume of syrup.

60. The process as set forth in claim 57, wherein the temperature of said syrup is from about 60° C. to 72° C.

61. The process as set forth in claim 57, wherein said polyelectrolyte is a polyacrylamide polyelectrolyte.

62. The process as set forth in claim 57, wherein said catalase is a beef liver catalase.

* * * * *